US008901188B2

(12) United States Patent
Karandikar et al.

(10) Patent No.: US 8,901,188 B2
(45) Date of Patent: Dec. 2, 2014

(54) ANTIMICROBIAL POLYURETHANE FOAM AND PROCESS TO MAKE THE SAME

(75) Inventors: Bhalchandra M. Karandikar, Beaverton, OR (US); Bruce Lance Gibbins, Lake Oswego, OR (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 394 days.

(21) Appl. No.: 13/493,209

(22) Filed: Jun. 11, 2012

(65) Prior Publication Data

US 2012/0322903 A1    Dec. 20, 2012

Related U.S. Application Data

(60) Provisional application No. 61/497,840, filed on Jun. 16, 2011.

(51) Int. Cl.
| | | |
|---|---|---|
| C08L 75/04 | (2006.01) | |
| A01N 59/16 | (2006.01) | |
| C08J 9/228 | (2006.01) | |
| B82Y 30/00 | (2011.01) | |
| A01N 25/10 | (2006.01) | |
| A01N 25/34 | (2006.01) | |

(52) U.S. Cl.
CPC .............. *A01N 59/16* (2013.01); *A01N 25/10* (2013.01); *A01N 25/34* (2013.01)
USPC ........................................................ 521/170

(58) Field of Classification Search
CPC ....... A01N 59/16; A01N 59/20; A01N 25/16; A01N 25/34; C08K 5/0058; C08J 9/0052; C08G 18/16; C08G 2101/00; C08G 2101/0008; C08G 2101/0016
USPC ........................................................ 521/170
See application file for complete search history.

(56) References Cited

U.S. PATENT DOCUMENTS

| | | | | |
|---|---|---|---|---|
| 4,842,932 | A * | 6/1989 | Burton | 428/375 |
| 4,937,273 | A | 6/1990 | Okuyama et al. | |
| 5,607,683 | A * | 3/1997 | Capelli | 424/405 |
| 5,662,913 | A * | 9/1997 | Capelli | 424/405 |
| 6,093,414 | A | 7/2000 | Capelli | |
| 6,555,228 | B2 * | 4/2003 | Guritza | 428/414 |
| 7,462,590 | B2 * | 12/2008 | Tichy et al. | 510/372 |
| 7,863,264 | B2 * | 1/2011 | Vange et al. | 514/184 |
| 8,203,029 | B2 * | 6/2012 | Gibbins et al. | 602/48 |
| 8,298,582 | B2 * | 10/2012 | Gastonguay et al. | 424/488 |
| 2007/0003603 | A1 * | 1/2007 | Karandikar et al. | 424/443 |
| 2007/0207335 | A1 * | 9/2007 | Karandikar et al. | 428/560 |
| 2010/0196487 | A1 * | 8/2010 | Voss et al. | 424/489 |
| 2011/0195105 | A1 * | 8/2011 | Nanos et al. | 424/409 |
| 2013/0122321 | A1 * | 5/2013 | Karandikar et al. | 428/553 |

FOREIGN PATENT DOCUMENTS

| | | |
|---|---|---|
| EP | 0010407 A1 | 4/1980 |
| EP | 1486523 A1 | 12/2004 |
| EP | 1817986 A2 | 8/2007 |
| EP | 2153722 A1 | 2/2010 |
| EP | 2253651 A1 | 11/2010 |
| EP | 2420521 A1 | 2/2012 |
| IT | MI2009A 000813 A1 | 11/2010 |
| WO | WO 00/09173 A1 | 2/2000 |
| WO | WO 03/097727 A1 | 11/2003 |
| WO | WO 2004/007595 A1 | 1/2004 |
| WO | WO 2006/015317 A2 | 2/2006 |
| WO | WO 2010/024890 A2 | 3/2010 |

OTHER PUBLICATIONS

Jain, Prashant and T. Pradeep, "Potential of Silver Nanoparticle-Coated Polyurethane Foam as an Antibacterial Water Filter," Biotechnology and Bioengineering, vol. 90, No. 1, Apr. 5, 2005, pp. 59-63.
Polyurethane, Römpp Lexikon Chemie 10, Auflage, Band 5, 1998, Georg Thieme Verlag, Stuttgart, New York, pp. 3512-3513.
Polyurethanes, Chapters 1-2, Ullmann's Encyclopedia of Industrial Chemistry, 6th edition, vol. 28, Wiley-VCH, 2003, pp. 667-669.
Santos, M. Soledade and Ester F.G. Barbosa, Silver (I) Complexation with Tertiary Amines in Toluene, Journal of the Chemical Society, Faraday Transactions, 1, vol. 84, No. 12, Jan. 1988, pp. 4439-4449.
Zinc Borate, product description, fire retardant, manufactured by Akrochem Corp, Akron, OH, Internet web page "http://www.akrochem.com/pdfs/fire/X-Zinc_Borate.pdf", Nov. 2007, 1 page.

* cited by examiner

*Primary Examiner* — Mike M Dollinger
(74) *Attorney, Agent, or Firm* — Karl V. Sidor

(57) ABSTRACT

An antimicrobial polyurethane foam that is formed from: a multi-functional isocyanate component; an aqueous polyol component reactive with the multi-functional isocyanate component; an antimicrobial metallic compound; and a complexing agent. The complexing agent is used to form a stable blend of the antimicrobial metallic compound with the polyol component. Exemplary complexing agents include amine compounds, ammonium-containing compounds and ammonia as well as combinations these compounds. The antimicrobial metallic compound can be a silver, zinc or copper compound. Desirably, the antimicrobial metallic compound is silver saccharinate. A process of making the antimicrobial polyurethane foam and stable blends used in the manufacture of the antimicrobial polyurethane foam are also disclosed.

18 Claims, 3 Drawing Sheets

ANTIMICROBIAL POLYURETHANE FOAM AND PROCESS TO MAKE THE SAME

This application claims the benefit of priority from U.S. Provisional Application No. 61/497,840 filed on Jun. 16, 2011.

FIELD OF THE INVENTION

The present invention relates to generally to foamed plastic materials and more particularly to foamed polyurethanes having antimicrobial properties.

BACKGROUND

The versatility and economics of flexible cellular foamed polyurethane materials (referred to as "polyurethane foams") have resulted in their adaptation for variety of uses including furniture cushioning, carpet underlayment, and cosmetic and medical applications such as absorbent wound dressings. In such application, it is desirable that dressing remain in place for several days to absorb the wound exudate and to minimize dressing changes to reduce the risk of trauma to the healing wound. It is also desirable that such foam wound dressing not support micro-organism growth but aid in lowering the bioburden. Thus, antimicrobial properties are very much desired in the foam material used in wound care applications.

There are several antimicrobial foam dressings in the market. Examples include PolyMem®, an antimicrobial foam dressing and Bio-Patch®, an antimicrobial site dressing. Silver is the active in the PolyMem® product and an organic compound is the active in the Bio-Patch® product. Considering the fact silver is broad spectrum antimicrobial and has been widely incorporated in a variety of wound care products, introducing silver into foam products have proved somewhat challenging. The difficulty of incorporating silver chemistries in foam products stems from its susceptibility to chemical reduction to metallic silver in the presence of polyurethane precursors. Post reduction, the presence of metallic silver imparts black or brown color to the foam such is the case with PolyMem® foam dressing.

In advancing the art, PCT International Publication WO 2004/007595 A1 by Lendell et al. for "Antimicrobial Polyurethane Foam" describes flexible polyurethane foam (i.e., foamed polyurethane) that incorporates a silver-based antimicrobial agent in the form of silver sodium hydrogen zirconium phosphate available as Antimicrobial AlphaSan® from Milliken Chemical of Spartanburg, S.C. This material may be mixed in with a polyisocyanate (i.e., multi-functional isocyanate) component or a polyol component (or both) prior to reaction.

One disadvantage with silver sodium hydrogen zirconium phosphate is that silver is not readily available for antimicrobial action. A large amount of the active agent is required to ensure a minimum efficacy threshold and to sustain long duration activity thus adding to the cost.

Accordingly, there is a need for improved antimicrobial polyurethane foam products. For example, there is a need for flexible cellular polyurethane foam products and flexible cellular hydrophilic polyurethane foam products that resist discoloration. This need extends to antimicrobial polyurethane foam products incorporating metal-based antimicrobial compositions. There is also a need for antimicrobial polyurethane foam products having a uniform distribution of metal-based antimicrobial compositions that resist discoloration.

SUMMARY

In response to the difficulties and problems discussed herein, the present inventors have discovered that certain antimicrobial compositions that comprise weakly soluble silver salt or a mixture thereof and silver nanoparticles when incorporated into foam products produced by the methods of the PCT International Publication WO 2004/007595 A1 provide foam products that are antimicrobial, resist discoloration in ambient light conditions and during sterilization processes.

The present invention thus provides antimicrobial compositions including an antimicrobial metallic compound in the form of a weakly soluble metal salt or a mixture a weakly soluble metal salt and metal nanoparticles for producing discoloration-resistant antimicrobial polyurethane foam. For example, the antimicrobial compositions including an antimicrobial metallic compound in the form of a weakly soluble silver salt or a mixture a weakly soluble silver salt and silver nanoparticles for producing discoloration-resistant antimicrobial polyurethane foam.

The present invention also provides methods of generating the antimicrobial compositions for producing antimicrobial polyurethane foams, the methods of making the antimicrobial polyurethane foams incorporating such antimicrobial compositions, and the antimicrobial foams produced.

Generally speaking, the antimicrobial compositions include a weakly soluble metal salt (e.g., silver salt) and metal nanoparticles (e.g., silver nanoparticles) and a solvent. Desirably, the solvent is water or a mixture where more than 50% by weight is water. Alternatively and/or additionally, the antimicrobial compositions may further include a soluble ammonia complex of the weakly soluble metal salt (e.g., silver salt). Antimicrobial compositions also further include a soluble ammonia complex of the weakly soluble metal salt (e.g., silver salt), metal nanoparticles (e.g., silver nanoparticles) and a solvent.

According to the invention, the complexing agent is used to solubilize the antimicrobial metallic compound in the solvent used. Exemplary complexing agents include amine compounds, ammonium-containing compounds and ammonia, ammonium hydroxide as well as combinations these compounds, though preferred complexing agent is ammonia.

The antimicrobial metallic compound can be a silver, zinc or copper compound. For example, the antimicrobial metallic compound may be copper, zinc or silver diazepine complexes, polymeric silver compounds, polymeric copper compounds, polymeric zinc compounds, copper compounds of saccharin, zinc compounds of saccharin, and silver compounds of saccharin. Desirably, the antimicrobial metallic compound is silver saccharinate.

The aqueous polyol component may be any conventional polyol used to form polyurethanes. Exemplary aqueous polyols include polyhydroxy-containing polyesters, polyoxyalkylene polyether polyols, polyhydroxy-terminated polyurethane polymers, polyhydroxy-containing phosphorus compounds, and alkylene oxide adducts of polyhydric polythioesters, polyacetals, aliphatic polyols and thiols, and mixtures thereof. Desirably, the aqueous polyol component is a polyether polyol.

The multi-functional isocyanate component may be any conventional multi-functional isocyanate used to form polyurethanes. Exemplary multi-functional isocyanates include toluene diisocyanate, monomeric methylene diisocyanate, polymeric methylene diisocyanate, and combinations thereof.

The composition may further include a chain extender. The chain extender may be an aromatic or aliphatic compound capable of reacting with at least two isocyanate terminated polymers units to form a polymer chain. Exemplary chain extenders may be aromatic or aliphatic compounds which are terminated with more than one hydroxyl or amine groups.

The present invention encompasses discoloration-resistant antimicrobial polyurethane foam that is the reaction product of: a multi-functional isocyanate component; an aqueous polyol component reactive with the multi-functional isocyanate component; an antimicrobial metallic compound complexed with a complexing agent and, optionally, silver nanoparticles.

The present invention also encompasses a process for producing discoloration-resistant antimicrobial polyurethane foam. The process includes the steps of: providing an aqueous polyol component; adding an antimicrobial metallic compound (e.g., one or more weakly soluble metal salts) and a complexing agent to form a complex that is soluble in the aqueous polyol component (alternatively and/or additionally, metal nanoparticles may be included with the soluble complex); solubilizing the antimicrobial metallic compound complex in the aqueous polyol component to form a stable blend; mixing a multi-functional isocyanate component with the stable blend; and reacting the multi-functional isocyanate component with the aqueous polyol to form a polyurethane foam incorporating the antimicrobial metallic compound. A key distinguishing aspect of the process of making the antimicrobial polyurethane foam of the present invention is that despite being added as a complex with the complexing agent the antimicrobial metallic compound, it is present as substantially only the antimicrobial metallic compound in the finished foam (and/or as antimicrobial metal nanoparticles, if they were added).

In one embodiment of the invention, the isocyanate prepolymer (prepared by reacting multi-functional isocyanates with low molecular weight diols, triols, dialkylene glycols, trialkylene glycols or polyoxyalkylene glycols of molecular weights up to 8000) is mixed with an aqueous solution comprising a thickener (to impart increased hydrophilicity) and a surfactant (to adjust the foam characteristics), and an antimicrobial metallic compound (e.g., silver saccharinate) complexed with a complexing agent such as, for example, ammonia (and optionally, metal nanoparticles complexed with a complexing agent) to produce antimicrobial foam.

Preferred quantities of the thickener and the surfactant are less than about five percent (5%) by weight of the aqueous solution. Desirably, the pH of the aqueous solution is in the range of 8 to 11 with most desirably pH being around 10. The preferred amount of metal antimicrobial particles (e.g., silver present as nanoparticles) is from about 50 to about 10,000 parts per million (ppm) by weight based on the weight of the dry foam with most desirably amount being between about 50 to about 2000 ppm. Desirably, the amount of antimicrobial metallic compound (e.g., weakly soluble silver salt) in the finished foam is less than five percent (5%) by weight based on the weight of the dry foam with most desirably amount being less than one percent (1%) by weight based on the weight of the dry foam. Note by "dry foam" it is meant the finished foam which is substantially dry—but may actually contain a small amount of residual moisture, which usually is less than 5% by weight of the finished foam. For example, the amount of antimicrobial metallic compound (e.g., weakly soluble silver salt) in the finished foam may be from about 0% to about less than five percent (5%) by weight based on the weight of the dry foam. However, when antimicrobial metallic compound is absent in the foam (i.e. 0%), it should desirably still contain metal present as elemental nanoparticles having antimicrobial properties. Thus, the antimicrobial foam of the present invention as contemplated is never devoid of antimicrobial metal.

The anions associated with the metallic compound are those that are considered biocompatible in the ranges used and considered GRAS (generally regarded as safe) by the U.S. FDA. The metal nanoparticles such as silver nanoparticles used in the antimicrobial polyurethane foam are generally smaller than 100 nm; most preferably their average diameter in the range of 5 to 50 nm. The preferred shape of the silver nanoparticles used in the foam of the present invention is spheroidal. However, silver nanoparticles of shapes other than spheroidal are encompassed by the present invention.

According to an aspect of the present invention, there is provided an antimicrobial polyurethane foam including silver nanoparticles (e.g., average diameter between 5 and 50 nm) that imparts a permanent color of the visible portion of the UV-VIS spectrum without the use of a colorant (such as, for example, dyes or pigments) and that the color is not inherent to the reactive components used to produce the foam or is attributed to other additives or ingredients present in the foam. Optionally, the polyurethane foam having color may be made without the presence of antimicrobial metallic compound (i.e., the foam may incorporate only metal nanoparticles such as silver nanoparticles as the metal-based antimicrobial material). Such foam may be less effective as antimicrobial material but may possess sufficient activity to be bacteriostatic and may find applications as filler material for cushions, pillows and as an odor absorbing matrix.

Yet another aspect of the present invention provides a method of imparting to the antimicrobial polyurethane a permanent color of the visible portion of the UV-VIS spectrum without the use of a colorant (known as dye or pigment) and that the color is not inherent to the reactive components used to produce the foam or is attributed to other additives in the foam, by the use of the nanoparticles of silver and generally by the use of nanoparticles of heavy metals.

In yet another aspect, the present invention provides an antimicrobial polyurethane foam that is hydrophilic, absorbent, contains plurality of open cells, is light weight, is reasonably resistant to discoloration by ambient light and is resistant to the discoloration induced by sterilization processes such as ethylene oxide (ETO) and electron beam (E-beam) irradiation.

Yet another aspect of the present invention is to provide polyurethane foam that sustains antimicrobial activity against gram positive bacteria, gram negative bacteria and fungi for more than 7 days by releasing therapeutically effective amount of metal ions such as ionic silver.

Yet another aspect of the present invention is to provide a suitable method of incorporating antimicrobial metallic compounds to effect more uniform distribution of the said compound within the foam matrix during the process of making antimicrobial polyurethane foam.

Other objects, advantages and applications of the present disclosure will be made clear by the following detailed description.

DETAILED DESCRIPTION

Figure 1:
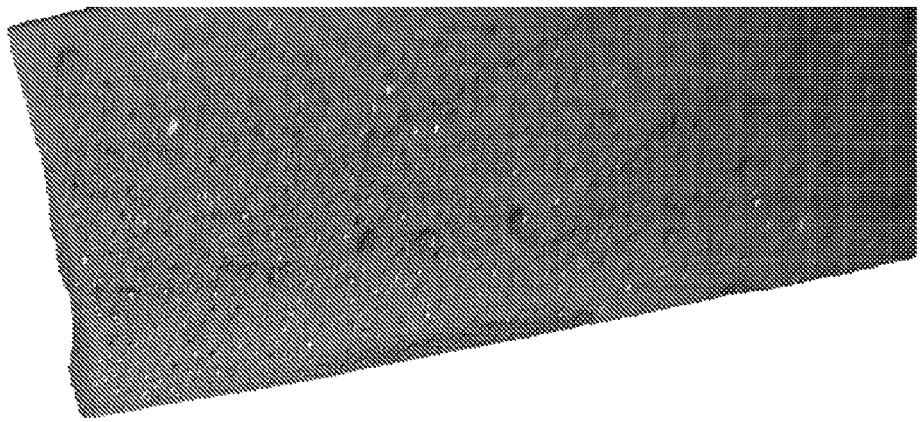
FIG. 1 is a black and white photograph illustrating samples of exemplary antimicrobial polyurethane foam containing silver nanoparticles after sterilization by electron beam irradiation and ethylene oxide techniques and a control sample.
Figure 1:
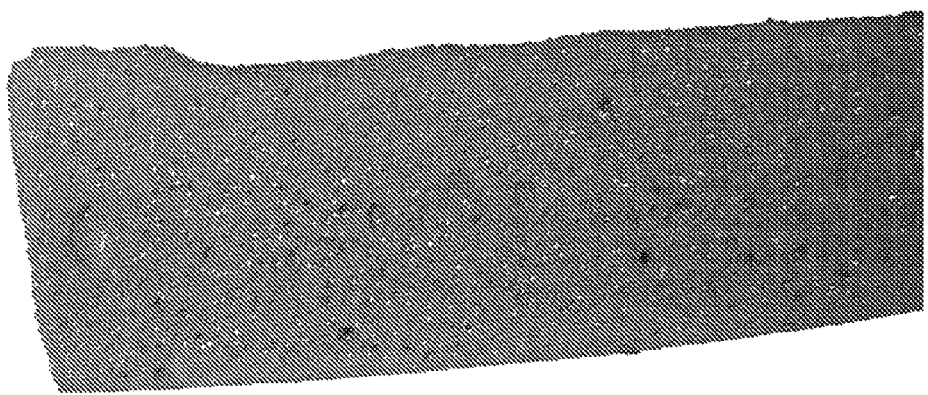
Figure 1:
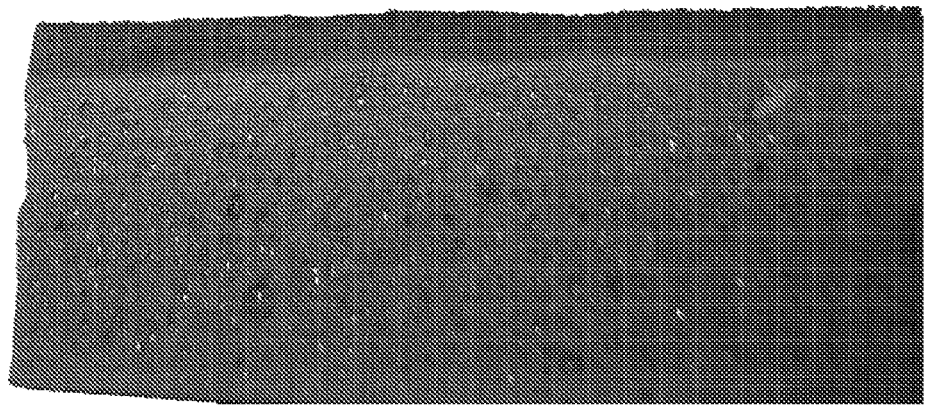

Reference will now be made in detail to one or more embodiments of the invention. It should be understood that features illustrated or described as part of one embodiment may be used with another embodiment to yield still a further embodiment. It is intended that the claims include these and other modifications and variations as coming within the scope and spirit of the disclosure.

As used herein, the term "complexing agent" refers to a substance that forms a complex compound with another material in solution. Exemplary complexing agents provide ions or molecules (also called ligands) that bind to a central metal atom. Ligands may be generated from amines, ammonia containing compounds, ammonia, phosphines, CO, $N_2$ and alkenes. Though, ligands with ammonia are preferred.

As used herein, the term "discoloration" refers to changes in color levels measured and recorded CIELAB coordinates using a Hunter Lab Color Difference Meter, Model D25 Optical Sensor and manufactured by Hunter Associates Laboratory, Reston, Va. CIELAB coordinates are a system agreed upon in 1976 within the "Commission Internationale de l'Eclairage" or CIE. The coordinates are designated L*, a*, b*. The system uses a three axis opponent color scale assuming color is perceived in white to black (L*) or "lightness", green to red (a*), and yellow to blue (b*) sensations. L* varies from 100 for a perfect white to zero for a perfect black. a* measures redness when plus (i.e., positive), grey when zero, and greenness when minus (i.e., negative). b* measures yellowness when plus (i.e., positive), grey when zero, and blueness when minus (i.e., negative).

As used herein, the term "discoloration-resistant" refers to the ability of a material to avoid meaningful changes in CIELAB color levels in comparison to similar conventional materials under essentially identical conditions such as, for example, exposure to a conventional ethylene oxide sterilization cycle or electron beam irradiation sterilization cycle. For example, an antimicrobial polyurethane foam containing from about one percent (1%) by weight silver saccharinate powder based on the dry weight of the foam may avoid meaningful changes in CIELAB color levels in comparison to an antimicrobial polyurethane foam containing about one percent (1%) by weight Antimicrobial AlphaSan® based on the dry weight of the foam after exposure to a conventional ethylene oxide sterilization cycle or electron beam irradiation sterilization cycle.

As used herein, the term "resistant to discoloration by light" refers to the ability of a material to avoid meaningful changes in CIELAB color levels in comparison to similar conventional materials under essentially identical conditions such as exposure to light of a specified wavelength or to ambient light for a specified length of time. For example, an antimicrobial polyurethane foam containing from about one percent (1%) by weight silver saccharinate powder based on the dry weight of the foam may avoid meaningful changes in CIELAB color levels in comparison to an antimicrobial polyurethane foam containing about one percent (1%) by weight Antimicrobial AlphaSan® based on the dry weight of the foam after exposure to ambient light for two (2) hours.

As used herein, the term "stable blend" refers to a mixture including a solvent or mixture of solvents, polyol, and actives (antimicrobial metallic compound as complex with complexing agent and elemental nanoparticles) that remains homogeneous (as single phase) for approximately at least for 24 hours at normal room temperature (approximately 25° C.). The mixture may further include one or more thickeners, surfactants and combinations thereof.

As used herein, the term "foam" refers to foamed plastic materials (also sometimes called "cellular plastics", "cellular polymers", "plastic foams" or "expanded plastics") and more specifically refers to plastic materials in which the apparent density is decreased by the presence of numerous cells disposed throughout its mass. Such materials are two-phase gas-solid systems in which the solid is continuous and composed of a polymer. Desirably, the cells are interconnected in such a manner that gas or liquid can pass from one to another—such materials are referred to as open cell and/or reticulated materials. Foams may be rigid or flexible. One exemplary standard test that may be used to characterize the flexibility of foams is ASTM D1566-10e1 "Standard Terminology Relating to Rubber".

As used herein, the term, "antimicrobial" refers to a substance that kills or inhibits the growth of microorganisms. Exemplary antimicrobial materials include metal ions that are eluted from metal particles. Such materials may exhibit antimicrobial properties when used at sufficiently high concentrations and/or with agents that enhance elution of ions and/or inhibit the deactivation of the ions.

The present invention provides a composition for producing antimicrobial foamed plastic materials. Generally speaking, these antimicrobial foamed plastic materials are made from polyurethane that incorporate one or more antimicrobial metallic compounds in the form of a weakly soluble metal salt(s) or a mixture a weakly soluble metal salt(s) and metal nanoparticles. Desirably, these materials produce discoloration-resistant antimicrobial polyurethane foam.

Generally speaking, the composition includes a multi-functional isocyanate component; an aqueous polyol component reactive with the multi-functional isocyanate component; an antimicrobial metallic compound; and a complexing agent.

According to the invention, the complexing agent is used to solubilize the antimicrobial metallic compound in the solvent used for the composition. That is, the complexing agent forms a complex with the antimicrobial metallic compound such that the complex is soluble in the solvent used for the composition. Exemplary complexing agents include amine compounds, ammonium-containing compounds (including but not limited to ammonium hydroxide) and ammonia as well as combinations these compounds. It is contemplated that phosphines, CO, $N_2$ and alkenes may also be used. Though, the preference for ligands with ammonia or ammonium containing compounds.

The antimicrobial metallic compound can be a silver, zinc or copper compound such as, for example, one or more weakly soluble metal salts. For ease of reference, silver will be used herein, but it is to be understood that any one of the three metals is intended. The antimicrobial metallic compound may be silver diazepine complexes, polymeric silver compounds, and silver compounds of saccharin. Desirably, the antimicrobial metallic compound is silver saccharinate.

By weakly soluble metallic salt or compound, it is meant those salts that generally have solubility in water at 25° C. of 10 grams per liter or less. However, salts having higher aqueous solubility may also be used in the practice of the present invention.

In addition to the antimicrobial metallic compound that interacts with the complexing agent to form a complex that is soluble in the solvent for the composition, metal nanoparticles (e.g., silver nanoparticles) may optionally be added to the composition as noted above. A thin metal oxide coating typically forms on the surface of such metal nanoparticles such that the oxide layer is capable of forming a water soluble complex with the complexing agent. While the inventors should not be held to a particular theory of operation, these water soluble complexes (i.e., complexes incorporating the antimicrobial metallic compound and, optionally, the metal nanoparticles) allow for excellent dispersion of the antimicrobial metallic compound and metal nanoparticles throughout the foamed plastic when properly mixed with the foam ingredients.

In one embodiment of the invention, the antimicrobial metallic compound and the elemental nanoparticles may not be derived from the same metallic element. For example, the antimicrobial metallic compound may be a silver based salt or a compound and the metallic nanoparticles may be of copper and/or zinc. In an alternate embodiment, the metallic compound or salt may be copper and/or zinc based whereas the elemental nanoparticles may be made of silver. Both combinations are encompassed by the present invention.

The aqueous polyol component may be any conventional polyol used to form polyurethanes. The polyol component is desirably composed of one or more polyol compounds. If a hydrophilic polyurethane foam product is desired, the aqueous solution component is desirably composed of water and one or more polyol compounds, such that at least 50% of the hydroxyl (—OH) functional groups of the polyol component are secondary hydroxyl groups.

Exemplary aqueous polyols include polyhydroxy-containing polyesters, polyoxyalkylene polyether polyols, polyhydroxy-terminated polyurethane polymers, polyhydroxy-containing phosphorus compounds, and alkylene oxide adducts of polyhydric polythioesters, polyacetals, aliphatic polyols and thiols, and mixtures thereof. Desirably, the aqueous polyol component is a polyether polyol.

The polyether polyol composition may desirably contain a predominant amount of secondary hydroxyl groups, with a composition containing all secondary hydroxyl groups being preferred. By a predominant amount of secondary hydroxyl group containing polyether polyol composition, it is meant that at least fifty weight percent of the hydroxyl groups should be secondary hydroxyl groups such as those derived from propylene oxide.

Methods of making polyether polyols are well known and include those polyethers prepared from the base catalyzed addition of an alkylene oxide such as, but not limited to ethylene oxide, propylene oxide or butylenes oxide, preferably ethylene oxide, to an initiator molecule containing, on the average, two or more active hydrogens. The polyalkylene polyether polyols are well known in the art and may be prepared by any known process, Examples of initiator molecules include, without limitation, diethylene glycol, ethylene glycol, dipropylene glycol, propylene glycol, trimethylene glycol, 51,2-butanediol, 1,3-butanediol, 1,4-butanediol, 1,4-pentanediol, 1,5-pentanediol, 1,6-hexanediol, 1,7-heptanediol, glycerine, 1,1,1-trimethyolpropane, 1,1,1 trimethylolethane, 1,2,6-hexantriol, or triethylolpropane.

The multi-functional isocyanate component may be any conventional multi-functional isocyanate used to form polyurethanes. Exemplary multi-functional isocyanates include toluene diisocyanate, monomeric methylene diisocyanate, polymeric methylene diisocyanate, and combinations thereof. These multi-functional isocyanates are generally well known in the art, and include, without limitation, 4,4'-, 2,4'-, and 2 2'-diphenylmethane diisocyanate, various polyphenylenepolymethylene multi-functional isocyanates (polymeric MDI), and mixtures of some or all of these compounds.

The multi-functional isocyanate component may also include one or more other aliphatic, cycloaliphatic, arylaliphatic, and/or aromatic multi-functional isocyanates. The multi-functional isocyanate component should desirably contain at least 80% by weight methylene diisocyanate (MDI) or polymeric methylene diisocyanate (MDI).

Modified multivalent isocyanates which are products obtained by the partial chemical reaction of organic diisocyanates and/or multi-functional isocyanates may be used. Examples include, without limitation, diisocyanates and/or multi-functional isocyanates containing ester groups, urea groups, biuret groups, allophanate groups, carbodiimide groups, isocyanurate groups, and/or urethane groups.

The composition may further include a chain extender. The chain extender may be an aromatic or aliphatic compound capable of reacting with at least two isocyanate terminated polymers units to form a polymer chain. Exemplary chain extenders may be aromatic or aliphatic compounds which are terminated with more than one hydroxyl or amine groups. These include compounds having at least two functional groups bearing active hydrogen atoms such as, but not limited to water, hydrazine, primary and secondary diamines, amino alcohols, amino acids, hydroxy acids, glycols, or mixtures thereof. An exemplary group of chain-extenders includes, without limitation, water, ethylene glycol, 1,4-butanediol and primary and secondary diamines which react more readily with the prepolymer than does water such as, but not limited to phenylene diamine, 1,4-cyclohexane-bis-(methylamine), ethylenediamine, diethylenetriamine, N-(2-hydroxylpropyl) ethylenediamine, N,N'-di(2-hydroxypropyl)ethylenediamine, piperazine, and 2-methylpiperazine.

The foamed polyurethane materials are generally prepared by the reaction of a polyoxyalkylene polyether polyol with an organic multi-functional isocyanate in the presence of a blowing agent and optionally in the presence of additional polyhydroxyl-containing components, chain-extending agents, catalysts, surfactants, stabilizers, dyes, fillers and pigments. Generally speaking, the reaction conditions to produce foamed polyurethane materials would be readily determined by one of ordinary skill in the art.

Any suitable catalysts or surfactants may be used, along with suitable processes for the preparation of cellular polyurethane foams as disclosed in U.S. Pat. No. Re. 24,514, the entire content of which is incorporated herein by reference, together with suitable machinery to be used in conjunction therewith. When water is added to generate carbon dioxide as blowing agent, corresponding quantities of excess isocyanate to react with water may be used. Such processes are generally referred to as conventional "pre-polymer processes" or "pre-polymer techniques".

It is contemplated that one may proceed with the preparation of the foamed polyurethane materials by a pre-polymer technique wherein an excess of organic multi-functional isocyanate is reacted in a first step with the polyol to prepare a pre-polymer having free isocyanate groups which is then reacted in a second step with water and/or additional polyol to prepare a foam. Alternatively, the components may be reacted in a single working step commonly known as the "one-shot" technique of preparing foamed polyurethane materials.

The present invention encompasses antimicrobial polyurethane foam that is the reaction product of: a multi-functional isocyanate component; an aqueous polyol component reactive with the multi-functional isocyanate component; an antimicrobial metallic compound that may desirably be resistant to discoloration by light; and a complexing agent. The materials used to prepare the antimicrobial polyurethane foam are as generally described above. The antimicrobial polyurethane foam may further include antimicrobial metal nanoparticles or, in some versions, the antimicrobial metal nanoparticles may be used instead of the antimicrobial metallic compound.

Desirably, the amount of antimicrobial metallic compound (e.g., weakly soluble silver salt) in the finished foam is less than five percent (5%) by weight based on the weight of the dry foam with the most desirable amount being less than one percent (1%) by weight based on the weight of the dry foam. Note by "dry foam" it is meant the finished foam which is at least substantially dry—but may actually contain a small amount of residual moisture, which usually is less than 5% by weight of the finished foam. For example, the amount of antimicrobial metallic compound (e.g., weakly soluble silver salt) in the finished foam may be from about 0% about less than five percent (5%) by weight based on the weight of the dry foam. However, when antimicrobial metallic compound is absent in the foam (i.e. 0%), it may still contain metal present as elemental nanoparticles having antimicrobial properties. Thus, the antimicrobial foam of the present invention as contemplated is never devoid of antimicrobial metal.

The anions associated with the metallic compound are those that are considered biocompatible in the ranges used and considered GRAS (Generally Regarded As Safe) by the U.S. Food and Drug Administration. If antimicrobial metal nanoparticles are incorporated in the antimicrobial polyurethane foam, the metal nanoparticles such as, for example, silver nanoparticles are generally smaller than 100 nm; most preferably their average diameter in the range of 5 to 50 nm. The preferred shape of the silver nanoparticles used in the foam of the present invention is spheroidal. However, silver nanoparticles of shapes other than spheroidal are encompassed by the present invention. The preferred amount of metal antimicrobial particles (e.g., silver present as nanoparticles) is from about 50 to about 10,000 parts per million (ppm) by weight based on the weight of the dry foam with most desirable amount being between about 50 to about 2000 ppm.

The present invention also encompasses a process for producing antimicrobial polyurethane foam. Desirably, the process produces antimicrobial polyurethane foam that is discoloration resistant. The process includes the steps of: providing an aqueous polyol component; adding an antimicrobial metallic compound (e.g., one or more weakly soluble metal salts) and a complexing agent to form a complex that is soluble in the aqueous polyol component (alternatively and/or additionally, metal nanoparticles may be included in the soluble complex); solubilizing the antimicrobial metallic compound complex in the aqueous polyol component to form a stable blend; mixing a multi-functional isocyanate component with the stable blend; and reacting the multi-functional isocyanate component with the aqueous polyol to form a polyurethane foam incorporating the antimicrobial metallic compound.

In an aspect of the invention, the process further includes the step of allowing the complexing agent to dissipate such that the antimicrobial metallic compound is present as substantially only the antimicrobial metallic compound in the finished foam (and/or as antimicrobial metal nanoparticles, if they were added).

According to an aspect of the invention, the complexing agent may be a catalyst for the reaction of the multi-functional isocyanate component with the aqueous polyol. Desirably, the complexing agent will be ammonia or an ammonium-containing compound. Furthermore, the process may include the step of adding a chain extender.

In one embodiment of the invention, the isocyanate prepolymer (prepared by reacting polyisocyanates with low molecular weight diols, triols, dialkylene glycols, trialkylene glycols or polyoxyalkylene glycols of molecular weights up to 8000) is mixed with an aqueous solution including a thickener (which may be used to impart increased hydrophilicity) and a surfactant (which may be used to adjust the foam characteristics), and an antimicrobial metallic compound (e.g., silver saccharinate) complexed with a complexing agent such as, for example, ammonia (and optionally, metal nanoparticles complexed with a complexing agent) to produce antimicrobial foam.

Preferred quantities of the thickener and the surfactant are less than about five percent (5%) by weight of the aqueous solution. Desirably, the pH of the aqueous solution is in the range of 8 to 11 with most desirably pH being around 10.

Another aspect of the present invention addresses a method for producing a stable blend used in the manufacture of antimicrobial polyurethane materials. The method includes the steps of: providing an aqueous polyol component; adding an antimicrobial material selected from antimicrobial metallic compounds, antimicrobial metal nanoparticles and mixtures thereof, and a complexing agent to forms a complex that is soluble in the aqueous polyol; and solubilizing the antimicrobial metallic compound complex in the aqueous polyol component to form a stable blend.

According to the method, the complexing agent may be amine compounds, ammonium-containing compounds and ammonia, and combinations thereof; and the complexing agent may further serve as a catalyst for the reaction of the aqueous polyol component and a multi-functional isocyanate component.

According to an aspect of the present invention, there is provided an antimicrobial polyurethane foam including silver nanoparticles (e.g., average diameter between 5 and 50 nm) that imparts a permanent color of the visible portion of the UV-VIS spectrum without the use of a colorant (such as, for example, dyes or pigments) and that the color is not inherent to the reactive components used to produce the foam or is attributed to other additives or ingredients present in the foam. Optionally, the polyurethane foam having color may be made without the presence of antimicrobial metallic compound (i.e., the foam may incorporate only metal nanoparticles such as silver nanoparticles as the metal-based antimicrobial material). Such foam may be less effective as antimicrobial material but may possess sufficient activity to be bacteriostatic and may find applications as filler material for cushions, pillows and as an odor absorbing matrix.

Yet another aspect of the present invention provides a method of imparting to the antimicrobial polyurethane a permanent color of the visible portion of the UV-VIS spectrum without the use of a colorant (known as dye or pigment) and that the color is not inherent to the reactive components used to produce the foam or is attributed to other additives in the foam, by the use of the nanoparticles of silver and generally by the use of nanoparticles of heavy metals.

In yet another aspect, the present invention provides an antimicrobial polyurethane foam that is hydrophilic, absorbent, contains plurality of open cells, is light weight, is reasonably resistant to discoloration by ambient light and is resistant to the discoloration induced by sterilization processes such as ethylene oxide (ETO) and electron beam (E-beam) irradiation.

Yet another aspect of the present invention is to provide polyurethane foam that sustains antimicrobial activity against gram positive bacteria, gram negative bacteria and fungi for more than 7 days by releasing therapeutically effective amount of metal ions such as ionic silver.

Yet another aspect of the present invention is to provide a suitable method of incorporating antimicrobial metallic compounds to effect more uniform distribution of the said compound within the foam matrix during the process of making antimicrobial polyurethane foam.

The present invention also encompasses antimicrobial foams composed of: a flexible matrix of polyurethane material defining a plurality of open cells; and an antimicrobial metallic salt and/or antimicrobial metal nanoparticles uniformly distributed throughout the matrix. This foam may be prepared utilizing the above-described processes and/or blends.

The present invention is further described by the examples which follow. Such examples, however, are not to be construed as limiting in any way either the spirit or the scope of the present invention.

EXAMPLES

All chemicals used in the examples described below were reagent grade unless specified otherwise.

Example 1

Lab Scale Preparation of Antimicrobial Silver Foam

Samples of generally hydrophilic polyurethane foam in the form of square slabs having approximate dimensions of about 10 inches×10 inches×1 inch in size and weighing approximately 150 grams each were prepared generally in accordance with the procedures set forth in PCT International Publication WO 2004/007595 A1 by Lendell et al. for "Antimicrobial Polyurethane Foam".

The foam slabs were prepared so they would contain an antimicrobial active agent in the form of silver at three target concentrations. The silver material elutes silver ions that provide antimicrobial activity and the concentrations of silver material generally corresponds to the level of antimicrobial activity. These target concentrations were 500, 1000 and 1500 ppm. The concentrations were achieved by adding either silver saccharinate powder or silver nanoparticles (or in some cases, both materials) to the ingredients used to make the polyurethane foam. The resulting foam slabs were tested for antimicrobial activity for 7 days.

To make the foam slab, de-ionized water (~180 ml), a compatible surfactant and a compatible polymeric thickener (each at a values less than 5% w/w) and the antimicrobial agent, either silver saccharinate or silver nanoparticles or mixtures thereof, were mixed in a disposable wax paper cup followed by a viscous polyurethane pre-polymer. The viscous mixture was quickly blended to uniformity using a high speed mixer (less than 1-2 minutes) and poured into a square shaped wax paper mold. Within minutes, the contents poured into the mold expanded as the mixture began to foam and cure. The mold was left undisturbed under very low light inside a ventilated hood for about 30 minutes. At this time, the cured foam mass was non-tacky to touch. The foam was removed from the mold and placed on a stack of disposable paper towels and heated in microwave oven for 5-10 minutes. The sample foam was then transferred to a conventional oven at 55° C. and thoroughly dried overnight. A control foam sample (Lendell Medisponge® 50P Hydrophilic Polyurethane Foam) was made the same way except the actives were left out.

The silver nanoparticles solution concentrate used in making the foam was made following a procedure described in Example 93 of the U.S. Patent Application Publication No. US 2007/0207335 A1 "Methods and Compositions for Metal Nanoparticle Treated Surfaces" published Sep. 6, 2007. The amount of each solution in the example was increased tenfold. The combined solution but without any parts to be coated was heated to 55° C. for 18 hours and cooled to room temperature. This solution was designated in Table 1 below as "regular M8" solution. The regular M8 solution was purified by a conventional dialysis method known to those ordinarily skilled in the art to remove all inorganic and organic low molecular weight impurities and designated as "pure M8".

The list of foam samples made, the active antimicrobial ingredient(s) and the amount of silver for each samples as calculated from the ingredients and as determined by conventional flame atomic absorption spectrophotometry (FAAS) techniques is presented in Table 1 "Antimicrobial Silver Foam Samples, Silver Content and ZOI (Zone of Inhibition) Assay Results". As is evident from the results, there is considerable variability in the amount of antimicrobial silver observed for the foam samples. It is generally believed this variability may be due to the operator (but only for the samples that contain silver nanoparticles) and may be due to the non-uniform distribution of silver saccharinate particles (for those samples that contain silver saccharinate particles). The variability in the amount of silver in the samples is believed to also be reflected in different durations of sustained antimicrobial activity seen for the samples tested.

The antimicrobial efficacy of sample foams was tested against three representative microorganisms (gram positive, gram negative and a fungus) which are identified as PSAE (*Pseudomonas aeruginosa*), Candida (*Candida albicans*) and MRSA (Methicillin-resistant *Staphylococcus aureus*). The data revealed none of the samples with 500 ppm Ag had much activity; the samples at 1000 ppm Ag had intermediate level activity and those at 1500 ppm had the most activity regardless of the form of silver—saccharinate salt, nanoparticles or a mix of the two. The results of this experiment led the inventors to conclude that 1500 ppm of Ag was likely to sustain the desired level of release of ionic silver (for lethal antimicrobial activity) for at least 5 days. For the samples of silver-containing foam described in Example 2 below, a nominal target of 1500 ppm of silver in the foam (on dry weight basis) was established.

TABLE 1

Antimicrobial Silver Foam Samples, Silver Content and ZOI Assay Results

| Sample # | Sample Type | ppm Ag Theor. | ppm Ag Meas. | PSAE | Candida | MRSA |
|---|---|---|---|---|---|---|
| | | | | Last Day of Observed Zone | | |
| 3 | Regular M8 | 500 | 690 ± 62 | None | 1/2 Day 5 | None |
| 4 | Regular M8 | 1000 | 1438 ± 129 | None | None | None |
| 5 | Regular M8 | 1500 | 2378 ± 145 | 2/2 Day 2 | 1/2 Day 7 | None |
| 6 | AgSacc | 500 | 129 ± 23 | None | 2/2 Day 1 | None |

TABLE 1-continued

Antimicrobial Silver Foam Samples, Silver Content and ZOI Assay Results

| Sample # | Sample Type | ppm Ag Theor. | ppm Ag Meas. | PSAE | Candida | MRSA |
|---|---|---|---|---|---|---|
| | | | | | Last Day of Observed Zone | |
| 7 | AgSacc | 1000 | 803 ± 129 | 1/2 Day 2 | 2/2 Day 5 | None |
| 8 | AgSacc | 1500 | 1187 ± 219 | 2/2 Day 5 | 1/2 Day 5 | None |
| 9 | AgSacc (Lot 2) | 500 | 387 ± 117 | None | 1/2 Day 2 | None |
| 10 | AgSacc (Lot 2) | 1000 | 852 ± 44 | 1/2 Day 5 | 1/2 Day 6 | None |
| 11 | AgSacc (Lot 2) | 1500 | 1395 ± 92 | 2/2 Day 7 | 2/2 Day 5 | None |
| 12 | Pure M8 | 500 | 512 ± 50 | None | None | None |
| 13 | Pure M8 | 1000 | 301 ± 373 | 1/2 Day 2 | 1/2 Day 5 | Outer side of foam down 0.5 mm ZOI |
| 14 | Pure M8 | 1500 | 1685 ± 47 | 1/2 Day 3 | None | None |
| 15 | Pure M8 + AgSacc | 167 + 333 | 596 ± 11 | None | 1/2 Day 2 | None |
| 16 | Pure M8 + AgSacc | 500 + 500 | 895 ± 41 | 1/2 zone Day 5 Outer side of foam down | 2/2 Day 5 | None |
| 17 | Pure M8 + AgSacc | 500 + 1000 | 1654 ± 105 | 2/2 Day 7 | 2/2 Day 5 | None |
| 18 | Reg. M8 + AgSacc | 167 + 333 | Not meas. | None | 1/2 Day 4 | None |

Note:
M8 is the ID for silver nanoparticles concentrate solution; AgSacc stands for silver saccharinate.

Example 2

Large Scale Preparation of Antimicrobial Silver Foam

After setting a theoretical target of 1500 ppm Ag for large scale production of polyurethane foam on the web in the form of rolls of foam sheet, machine trials were carried out at on large scale foam manufacturing equipment, the details and operation of which are well known to those of skill in the art. Another objective of the trials was to demonstrate that antimicrobial silver foam process was scalable (100 pounds or higher lot size on dry foam basis). The pertinent details of machine trials and the resulting data are presented in Table 2 "Production Trials of Antimicrobial Silver Foam" below.

TABLE 2

Production Trials of Antimicrobial Silver Foam

| Trial No. | Target Ag (ppm) | Foam size | Foam characteristics | Measured Ag (ppm) Note (2) |
|---|---|---|---|---|
| 1 | 1500 (1333 ppm as AgSacc* & 167 ppm as AgNP**) Note (1) | 1/8" and 3/16" thick and 13"-15" wide in rolls | Golden yellow, pliable and stretchable, open cell | ~400 ppm |
| 2 | 1500 (1333 ppm as AgSacc & 167 ppm as AgNP) | 1/8" and 3/16" thick and 13"-15" wide in rolls | Golden yellow, pliable and stretchable, open cell | ~860 ppm |
| 3 | 1500 (1333 ppm as AgSacc & 167 ppm as AgNP) | 1/8" and 3/16" thick and 13"-15" wide in rolls | Golden yellow, pliable and stretchable, open cell | ~960 ppm |

Note:
(1) *AgSacc = Silver saccharinate;
**AgNP = Silver nanoparticles concentrate;
Note:
(2) Silver in the foam analyzed by FAAS Three trials were attempted. Each successive trial was designed to include lessons learned from the previous trial. It was observed that the silver content of the foam from Trial #1 was much lower than the target value. After analyzing the test results, the conclusion was reached that the cause of lower silver content of the foam was not due to error in the FAAS analysis, but some deviation in the large scale production process. Despite adding the correct amount of silver in aqueous solution in the feed tank, it somehow was not getting incorporated into the foam. An observation was made that silver saccharinate particles were settling out of the aqueous solution and collecting at the mixing tank bottom during a 30 minute period when the aqueous solution was not stirred. This 30 minutes stoppage of the stirrer was required by the process equipment and could not be avoided.

Before carrying out Trial #2, a test was carried out to examine the extent of silver saccharinate settling by sampling the suspension of silver-containing ingredients over 30 minutes at fixed time intervals of 10 minutes after stirring was stopped. The sample aliquots were analyzed for silver and revealed they contained an average 1277 ppm Ag (0 minutes after stopping), 1126 ppm Ag (10 min), 1087 ppm Ag (20 min) and 1051 ppm Ag (30 min). The decreasing trend in the data was apparent (i.e. the silver saccharinate particles were settling out). Thus, a need to keep the particulate suspension stirred during the foam production was identified and changes to the production procedure were made. The Trial #2 was performed with the modified procedure. The resulting foam samples were analyzed for silver and still showed silver content much less (860 ppm) than the target value (1500 ppm Ag). Repeat analysis to account for all of the silver added to the aqueous solution indicated that while a uniform suspension may have been present in the tank, the silver saccharinate may have slowly settled out in the piping and may have been trapped on the in line filter used to keep dirt particles out.

The Trial #3 was designed to improve the outcome (i.e. increase the amount of silver in the finished foam product). One change made was to increase the viscosity of the aqueous solution that included the silver particles because it is well known that higher viscosity would increase the drag force on suspended particles and thus decrease their settling velocity. This in turn would increase settling time and keep more solids suspended. The viscosity of the aqueous solution was increased by doubling the amount of thickener polymer and Trial #3 was repeated as before. The silver analysis of the finished foam material still was much less than its target value (960 ppm vs. 1500 ppm). Collectively, the results of the 3 trials revealed the stirring of aqueous solution as it was fed to the web and increasing solution viscosity were not suitable approaches to meet the need for a robust solution for predictable silver foam target loading. For successful scale up of process for making antimicrobial silver foam, a robust solution was needed.

Example 3

Preparation of Antimicrobial Foam Using Silver Saccharin Ammonia Complex

In the samples made in previous two examples, silver saccharinate was dispersed in polyurethane foam in the form of fine particles. The results of the foam production trial revealed that the amount of silver in the foam could not be reliably controlled in the current process by modifying the process parameters such as stirring speed and viscosity. In order to overcome the settling of silver saccharinate particles, the silver saccharinate was dissolved in aqueous ammonium hydroxide solution to form soluble silver saccharinate ammonia complex. The complex solution with added thickener and surfactant was used to produce the polyurethane foam in accordance with the following general procedure. The surfactant and thickener are of the type known to those of skill in the art.

About 180 g of de-ionized water was transferred to a large disposable paper cup. To a 100 ml glass beaker, an amount of silver saccharinate wet cake to yield ~1333 ppm in the resulting foam (based on the dry weight of the foam) was added, followed by 20 g of de-ionized water and a few drops of surfactant known to those of skill in the art of making polyurethane foam. The contents in beaker were gently stirred for 15 minutes to re-suspend the solids and break up any chunks. Ammonia solution (9%) corresponding to an ammonia to silver molar ratio of 3 was added slowly to the silver saccharinate suspension until all the solids were dissolved. The pH of this solution was ~11.0. To the water in paper cup, surfactant (~0.3% w/w), thickener (~0.25% w/v) and a sufficient amount of silver nanoparticles concentrate to yield ~167 ppm in the resulting foam (based on the dry weight of the foam) were added under stirring to give an amber brown viscous solution.

The dilute silver saccharinate ammonia complex solution (in the glass beaker) was added to the viscous solution (in the cup) and mixed in to uniformity. A small amount of glacial acetic acid (about ¼ of the moles of ammonia added) was mixed to lower the pH from 11.0 back to a pH of approximately 9.0. Finally 150 g of polyurethane pre-polymer was added to the aqueous mixture under vigorous stirring and poured into a 10 inch×10 inch square wax paper mold. After 15 minutes, the non-tacky and wet foam was removed from the mold and dried in a conventional laboratory microwave oven by repeatedly heating and cooling for few minutes, and repeating the cycle numerous times. The golden yellow colored slab of foam about 1 to 2 inches thick was obtained.

Three samples from different parts of the foam slab were cut and analyzed for silver by FAAS techniques. For silver analysis by FAAS, the foam sample was digested in a mixture of 30% $HNO_3$ and 30% $H_2O_2$ overnight to obtain a low viscosity brown liquid. After additional dilution, the sample was analyzed by flame atomic absorption on a VARIAN 220S atomic absorption spectrometer (available from Varian Inc., which is now part of Agilent Technologies, Inc., Santa Clara, Calif.) that was calibrated using a set of known silver solution standards. The amounts of silver in the tree foam samples were 1256, 1276 and 1306 ppm respectively. These values are quite close to the theoretical target value of 1500 ppm indicating that the use of silver saccharinate ammonia complex (a water soluble form) was a better solution to solve the particulate suspension problem causing non-uniformity of silver in the foam matrix. This approach not only eliminated the particulate suspension once for all but also provided a robust method for producing antimicrobial silver foam with predetermined silver loadings.

Example 4

Measurement of Properties and Broad Spectrum Anti-Microbial Activity of Foam Made Utilizing Silver Saccharinate—Ammonia Complex Method Polyurethane foam slabs (~10"×10"×1") were made generally in accordance with the procedure outlined in Example 3. These foam slabs were prepared so they had silver contents of approximately 2500 ppm (Lot L11202008B) and approximately 4000 ppm (Lot 01292009), respectively. The samples cut from these slabs were used to assess the antimicrobial activity and to determine physical properties (density, water absorption etc).

Results of Antimicrobial Testing

Antimicrobial activity of the polyurethane foams was evaluated against clinical isolates of commonly implicated micro-organisms (gram positive, gram negative and fungi) in infections for efficacy and durability. The testing was carried out as described in the specification section. A commercially available antimicrobial foam product incorporating a silver antimicrobial material was used as a control sample. The commercially available antimicrobial foam product is available under the tradename Optifoam® Ag from Medline Industries, Inc. of Mundelein, Ill.

Efficacy test results are tabulated in the Table 3 "Antimicrobial Activity of Antimicrobial Silver Foam (Lot # L11202008B) Against 6×1 Clinical Isolates" and Table 4 "Antifungal Activity of Silver Foam (Lot # L11202008B) Against 2 Fungal Isolates" below. More than 99.99% reduction in bacterial count against all six isolates and greater than 99% reduction against two fungal isolates was seen despite very high initial inoculum levels (~$1e^6$ cfu/ml). The efficacy shown by the antimicrobial silver foam prototypes of the present invention match that of the commercial Optifoam® Ag. In the case of *Enterobacter cloacae* it actually performed better. Against fungi, the prototypes were slightly better than Optifoam® Ag. Thus, the antimicrobial foam of the present invention exhibited broad spectrum antimicrobial activity against bacteria and fungi.

The results of the durability testing are presented in Table 5 "Antimicrobial Efficacy of Antimicrobial Silver Foam Against *Pseudomonas Aeruginosa* (Lot # L11202008B)" and Table 6 "Antimicrobial Efficacy of Antimicrobial Silver Foam Against *Staphylococcus aureus* (MRSA) (Lot # L11202008B)". The test was carried out against one representative strain each of gram positive (*Staphylococcus aureus* MRSA) and gram negative bacteria (*Pseudomonas aeruginosa*) recovered from clinical settings. The duration of the test was 10 days at the end of which the samples were examined for antimicrobial efficacy.

The test data are considered remarkable in that the foam prototype after 7 days showed 99.99+% reduction against *Pseudomonas aeruginosa* and MRSA strains. The same activity level was maintained through 10 days against *Pseudomonas* but it dropped slightly to 99% against MRSA after 7 days through 10 days. In contrast, Optifoam® Ag exhibited 99.99% activity against *Pseudomonas* for 2 days and for one day against MRSA. Against MRSA, the inventive prototype foam performed consistently better than Optifoam® Ag.

The durability test results are extraordinary considering that Optifoam® Ag contains nearly 2.5 times more silver than 2500 ppm value in the foam sample tested.

A reasonable shelf life is expected for any antimicrobial silver foam product. Over that period, it must be storage stable and retain its required function. To assess that the foam prototypes made did not degrade in performance over time, tests of the antimicrobial property of freshly made sample foam and of the same sample foam after 180 days in real time. The results are listed in Table 7 "Antimicrobial Activity of Silver Foam (Lot # L01292009) Against Two Clinical Isolates After 180 Days". As can be seen, the foam maintained 99.99% reduction efficacy even after 180 days giving confidence that a 2 year shelf life for the inventive foam product is possible.

TABLE 3

Antimicrobial Activity of Antimicrobial Silver Foam (Lot # L11202008B) Against 6 X 1 Clinical Isolates

| Clinical isolate | Log of the Initial Inoculum | **Average Log growth in Optifoam ®-Ag (+ve ontrol) | **Average Log growth in AM silver PU foam | Average *Log reduction Optifoam ®-Ag (+ve ontrol) | Average *Log reduction AM silver PU foam | Average Percentage Reduction Optifoam ®-Ag (+ve ontrol) | Average Percentage Reduction AM silver PU foam |
|---|---|---|---|---|---|---|---|
| *Pseudomonas aeruginosa* | 5.99 | 1.00 | 1.00 | 4.99 | 4.99 | 99.9989 | 99.998 |
| *Staphylococcus epidermidis* | 5.81 | 1.00 | 1.00 | 4.81 | 4.81 | 99.9984 | 99.9984 |
| *Staphylococcus aureus* (MRSA) | 6.26 | 2.28 | 1.00 | 3.98 | 5.26 | 99.9894 | 99.9994 |
| *Enterobacter cloacae* | 5.88 | 5.12 | 1.00 | 0.76 | 4.88 | 82.6815 | 99.9986 |
| *Enterococcus faecalis* (VRE) | 6.00 | 1.00 | 1.00 | 5.00 | 5.00 | 99.9990 | 99.9990 |
| *Escherichia coli* | 6.15 | 1.00 | 1.00 | 5.15 | 5.15 | 99.9992 | 99.9992 |

TABLE 4

Antifungal Activity of Silver Foam (Lot # L11202008B) Against 2 Fungal Isolates

| Clinical isolate | Log of the Initial Inoculum | **Average Log growth in Optifoam ®-Ag (+ve ontrol) | **Average Log growth in silver PU foam | Average *Log reduction Optifoam ®-Ag (+ve ontrol) | Average *Log reduction silver PU foam | Average Percentage Reduction Optifoam ®-Ag (+ve ontrol) | Average Percentage Reduction silver PU foam |
|---|---|---|---|---|---|---|---|
| *Candida albicans* | 5.48 | 3.66 | 3.18 | 1.81 | 2.30 | 98.4675 | 99.4983 |
| *Rhodotorula glutinis* | 5.00 | 3.07 | 2.95 | 1.93 | 2.06 | 98.8267 | 99.1212 |

TABLE 5

Antimicrobial Efficacy Of Antimicrobial Silver Foam Against *Pseudomonas Aeruginosa* (Lot # L11202008B)

| Test points | Log of Initial Inoculum | **Average Log growth in Optifoam ®- Ag (+ve control) | **Average Log growth in AcryMed Antimicrobial silver PU foam | Average *Log reduction Optifoam ®- Ag | Average *Log reduction Antimicrobial silver PU foam |
|---|---|---|---|---|---|
| Day 1 | 5.54 | 1.00 | 1.00 | 4.54 | 4.54 |
| Day 2 | 5.84 | 1.00 | 1.00 | 4.84 | 4.84 |
| Day 3 | 5.49 | 2.84 | 1.00 | 2.65 | 4.49 |
| Day 4 | 5.62 | 4.88 | 1.00 | 0.74 | 4.62 |
| Day 5 | 6.00 | 5.61 | 1.00 | 0.39 | 5.00 |
| Day 6 | 5.98 | 5.74 | 1.00 | 0.25 | 4.98 |
| Day 7 | 6.02 | 6.00 | 1.00 | 0.02 | 5.02 |
| Day 8 | 5.80 | 5.80 | 1.00 | 0 | 4.80 |
| Day 10 | 5.44 | 1.00 | 1.00 | 4.44 | 4.44 |

TABLE 6

Antimicrobial Efficacy of Antimicrobial Silver Foam Against *Staphylococcus aureus* (MRSA) (Lot # L11202008B)

| Test points | Log of Initial Inoculum | **Average Log growth in Optifoam ®- Ag (+ve control) | **Average Log growth in AcryMed Antimicrobial silver PU foam | Average *Log reduction Optifoam ®- Ag | Average *Log reduction Antimicrobial silver PU foam |
|---|---|---|---|---|---|
| Day 1 | 5.78 | 1.00 | 1.00 | 4.78 | 4.78 |
| Day 2 | 5.91 | 2.71 | 1.00 | 3.20 | 4.91 |
| Day 3 | 5.80 | 2.28 | 1.00 | 3.52 | 4.80 |
| Day 4 | 6.31 | 2.28 | 1.00 | 4.03 | 5.31 |
| Day 5 | 6.08 | 2.90 | 1.00 | 3.18 | 5.08 |
| Day 6 | 6.04 | 3.07 | 1.00 | 2.97 | 5.04 |
| Day 7 | 6.18 | 3.33 | 1.00 | 2.84 | 5.18 |
| Day 8 | 6.14 | 4.14 | 3.14 | 2.00 | 3.00 |
| Day 10 | 6.19 | 5.22 | 3.59 | 0.97 | 2.60 |

TABLE 7

Antimicrobial Activity of Silver Foam (Lot # L01292009) Against Two Clinical Isolates After 180 Days

| Clinical isolate | Log of the Initial Inoculum | **Average Log growth in Optifoam ®-Ag (+ve ntrol) | **Average Log growth in AM silver PU foam | Average *Log reduction Optifoam ®-Ag (+ve ontrol) | Average *Log reduction AM silver PU foam | Average Percentage Reduction Optifoam ®-Ag (+ve ontrol) | Average Percentage Reduction AM silver PU foam |
|---|---|---|---|---|---|---|---|
| *Pseudomonas aeruginosa* | 6.20 | 4.89 | 1.00 | 1.31 | 5.20 | 95.1403 | 99.9993 |
| *Staphylococcus aureus* (MRSA) | 6.15 | 1.00 | 1.00 | 5.15 | 5.15 | 99.9992 | 99.9992 |

*Log reduction: (Log of initial inoculum) − (Log survivors in the silver foam samples). Values represent the log reduction in duplicate assays at each test point.
**Average Log values of 1.00 are reported indicating that counts between 1-25 cfu/ml for a particular dilution is considered insignificant. A statistically significant bacterial count is said to be in the range of 25-250 CFU/ml at a particular dilution.

Physical Property Measurements

Most pertinent physical properties of antimicrobial foam samples such as water or saline uptake, the foam density, color and the effect of sterilization (electron-beam irradiation and ethylene oxide) were measured. Water or saline absorbency is important as the foam material is often used to absorb exudate in wound care products. Thus sufficient absorbency is essential to prevent leaks. In water absorbency or hydration test of the foam, a sample piece was weighed before and after soaking in water or saline for 1 hour at normal room temperature (approximately 25° C.). From the change in weight, the foam absorbency or hydration was calculated as % based on its original weight as grams of water or saline/grams of dry foam.

TABLE 8

Hydration of Silver Foam After 6 Months Lot L01292009 (n = 3)

| Time (days) | % Hydration | St dev |
|---|---|---|
| 0 | 1229.8 | 51.01 |
| 180 | 1115.2 | 124.94 |

The results in Table 8 "Hydration of Silver Foam After 6 Months Lot L01292009 (n=3)" show the antimicrobial foam is a good absorbent material absorbing nearly ~12 times it weight in moisture. Its absorbency is not affected over time and is comparable for foams with and without silver present as well as with Optifoam® Ag (~11.5 g water/g foam).

Foam Density

This property is a measure of the porosity of the foam and related to the average size of the cell in the open cell foam matrix. To determine foam density, the dimensions x, y and z directions of known foam sample were measured to calculate the foam volume. From its weight and volume, the density was calculated in gm/cm$^3$. The results are presented in Table 9 "Foam Density Measurement Results". The foam material of the present invention was a sample from Trial #3, Example 2. The results indicate that the inventive foam material is almost 60% less dense than Optifoam® Ag. Visual examination of the two suggest that open cells in the prototype foam are larger than those in Optifoam® Ag.

TABLE 9

Foam Density Measurement Results

| ID | Foam Type | Volume (cm$^3$) | Mass (g) | ρ (g/cm$^3$) | Avg. ρ (g/cm$^3$) | StDev |
|---|---|---|---|---|---|---|
| 0121-02A1 | Optifoam ® Ag | 2.5806 | 0.5076 | 0.1967 | 0.1940 | 0.0028 |
| 0121-02A2 | | 2.5806 | 0.5010 | 0.1941 | | |

TABLE 9-continued

Foam Density Measurement Results

| ID | Foam Type | Volume (cm³) | Mass (g) | ρ (g/cm³) | Avg. ρ (g/cm³) | StDev |
|---|---|---|---|---|---|---|
| 0121-02A3 | | 2.5806 | 0.4931 | 0.1911 | | |
| 0121-02B1 | Ag Foam, | 1.8589 | 0.1482 | 0.0797 | 0.0782 | 0.0020 |
| 0121-02B2 | ⅛" Trial 3, | 1.9219 | 0.1460 | 0.0760 | | |
| 0121-02B3 | Example 2 | 2.0164 | 0.1593 | 0.0790 | | |

Foam Color

Over its suggested shelf life, the golden yellow color of the foam should remain essentially unchanged. This is especially true for silver containing medical products as they often undergo discoloration over time even if they are in stored in light impervious packages. A change in color could indicate loss of activity to a customer discouraging its use. The color of the foam material was quantified by measuring L, a*, b* co-ordinates at the start and after 180 days. During this period the sample was left undisturbed in a lab drawer. The L, a*, b* co-ordinates of the test foam sample are listed in Table 10 "Average L, a*, b* Color Co-Ordinates of Silver Foam (Lot # L01292009)". The difference in L, a*, b* values is minimal indicating that the sample essentially did not experience color change even after 180 days indicating good resistance to color change when kept protected from light.

TABLE 10

Average L, a*, b* Color Co-Ordinates of Silver Foam (Lot # L01292009)

| Time (days) | Foam Lot | L | a* | b* |
|---|---|---|---|---|
| 0 | L01292009 (n = 3) | 71.34 | 3.41 | 40.23 |
| 180 | same (n = 3) | 74.02 | 3.46 | 41.07 |

Example 5

Scaled Production of Antimicrobial Silver Foam Using Silver Saccharinate-Ammonia Complex After successfully producing antimicrobial silver foam using silver saccharinate-ammonia complex on small scale (slabs) and showing improvement in the uniform retention of silver in the foam (measured value of silver was within 15% of the target value; see Example 3 above), scaled up production of the silver foam was attempted on conventional polyurethane foam manufacturing equipment (i.e. machine trial). Because of the use of a water soluble form of silver saccharinate in the form of its ammonia complex, the problem associated with poor suspension of insoluble silver saccharinate particles was eliminated. Thus, during the machine trial all equipment and process steps were operated as if there was no suspended material in the aqueous solution. However, the aqueous solution was stirred for longer period than before (2 hours vs. 15 minutes) to ensure all insoluble silver saccharinate was converted to its soluble ammonia complex before the foaming step was begun.

Additionally, changes were made to the web speed and temperature settings of the curing and drying sections of the oven through which the web traveled. These changes ensured the foam exiting the oven was tack free and had the right amount of moisture. Following its exit, the foam was cooled to room temperature as it passed over a set of rollers and was rolled onto spools. Three rolls were made (front, middle and back) and each spool roughly held 100 ft. of foam.

Analysis of Foam Sheet Material

The foam sheet material from each roll was analyzed for silver. The silver values (average (n=3) ~3550 ppm) were found to be within 12% of the target value of 4000 ppm. This was considered a remarkable improvement over the results of earlier trials employing silver saccharinate particulate suspension to make the foam. The actual silver content of the foam from those trials averaged 36-43% less than the target value of 1500 ppm. Clearly, the approach of converting insoluble silver saccharinate to its soluble ammonia complex permitted a more robust process and thus produced foam whose silver content was closer to its target.

The finished foam sheet material did not emit any ammonia odor due to any residual silver salt ammonia complex form indicating that all of ammonia complex had reverted back to silver saccharinate. Further, de-ionized water (~50 ml) in which the foam sheet samples (~1 g weight) were immersed and repeatedly underwent several absorption and squeeze cycles at 25 C did not register alkaline pH (due to residual ammonia).

In a recent zone-of-inhibition (ZOI) assay, a foam sheet sample exhibited large zones of inhibition against *Pseudomonas aeruginosa* and MRSA after nearly 18 months in storage at room temperature protected from light. This clearly demonstrated excellent storage stability of the antimicrobial foam sheet material made in this example.

Example 6

Effect of Sterilization by ETO and E-Beam on the Antimicrobial Silver Foam

For the antimicrobial silver foam of the present invention to have commercial utility, it is important that it withstand conventional ethylene oxide (ETO) sterilization methods and conventional electron beam (E-beam) irradiation sterilization methods that are common in medical device industry. For example, any adverse effect such as drastic color or shade change post sterilization would not only affect its appearance (silver containing matrices tend to discolor or darken) but may affect its efficacy as well.

One inch wide and ~10" long strips of antimicrobial silver foam (Sample #4, #11 and #17 from Example 1) were sealed in ETO and E-beam compatible packages and sent out for sterilization at commercial sterilization facilities. Standard commercial ETO process and E-beam at ~25 KGy were carried out. The samples were returned and examined for appearance. No difference in color was observed between non-sterilized and sterilized samples.

Figure 2:
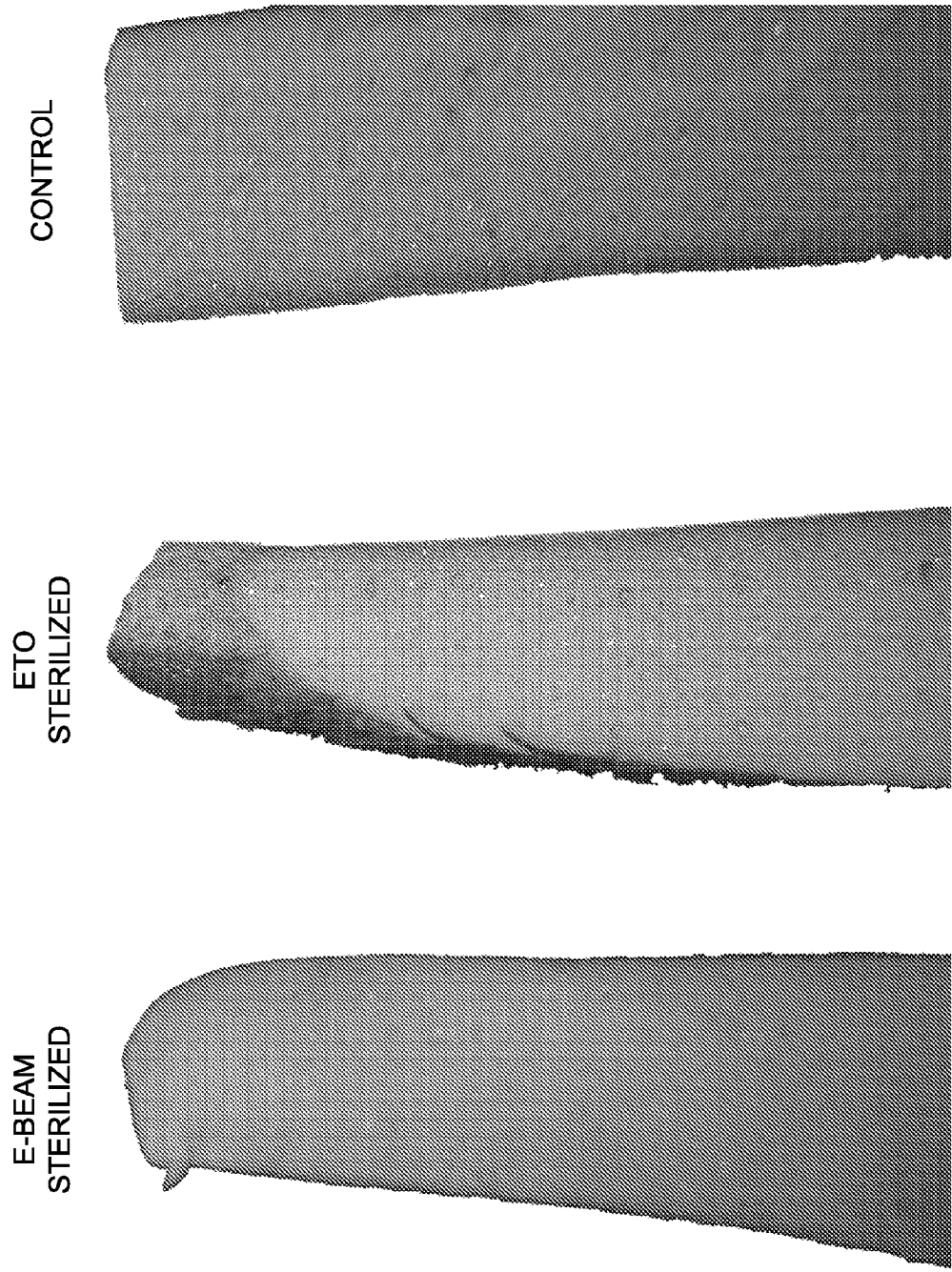
FIG. 2 is a black and white photograph illustrating samples of exemplary antimicrobial polyurethane foam containing silver saccharinate after sterilization by electron beam irradiation and ethylene oxide techniques and a control sample.
Figure 3:
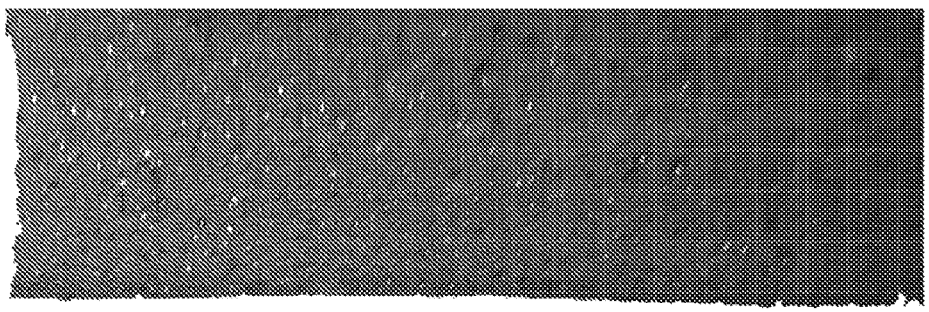
FIG. 3 is a black and white photograph illustrating samples of exemplary antimicrobial polyurethane foam containing both silver nanoparticles and silver saccharinate after sterilization by electron beam irradiation and ethylene oxide techniques and a control sample.
Figure 3:
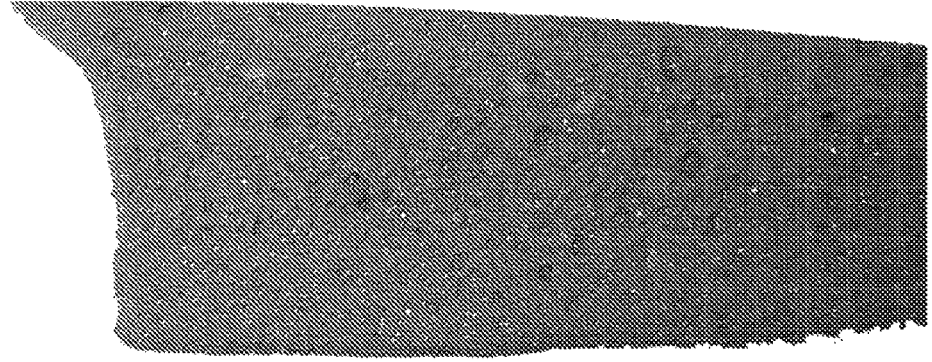
Figure 3:
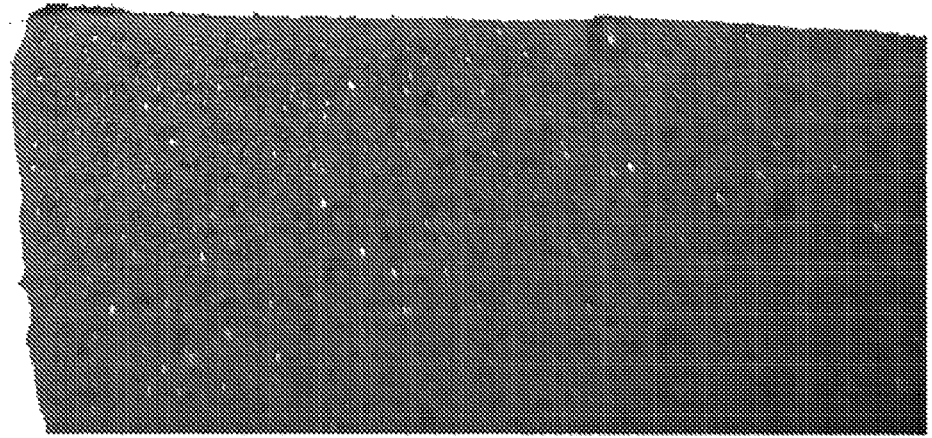

More particularly, FIG. 1 is a black and white photograph illustrating samples of antimicrobial polyurethane foam containing silver nanoparticles (Sample #4, Example 1) after sterilization by electron beam irradiation and ethylene oxide techniques and a control sample. FIG. 2 is a black and white photograph illustrating samples of antimicrobial polyurethane foam containing silver saccharinate (Sample #11, Example 1) after sterilization by electron beam irradiation and ethylene oxide techniques and a control sample. FIG. 3 is a black and white photograph illustrating samples of antimicrobial polyurethane foam containing both silver nanoparticles and silver saccharinate (Sample #17, Example 1) after sterilization by electron beam irradiation and ethylene oxide techniques and a control sample. As is evident from the black and white photographs, no significant difference in shade was observed between the control samples and the sterilized samples. Additionally, during inspection of the samples, no difference in color was observed between the control samples and the sterilized samples.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

We claim:

1. A process for producing an antimicrobial polyurethane foam comprising:
    providing an aqueous polyol component;
    adding an antimicrobial metallic compound and a complexing agent to form a complex that is soluble in the aqueous polyol component;
    solubilizing the antimicrobial metallic compound complex in the aqueous polyol component to form a stable blend;
    mixing a multi-functional isocyanate component with the stable blend;
    reacting the multi-functional isocyanate component with the aqueous polyol to form a polyurethane foam incorporating the antimicrobial metallic compound; and
    allowing the complexing agent to dissipate such that the antimicrobial metallic compound is present as substantially only the antimicrobial metallic compound in the finished foam.

2. The process of claim 1, wherein the antimicrobial metallic compound is a silver, zinc or copper compound.

3. The process of claim 1, wherein the complexing agent is selected from amine compounds, ammonium-containing compounds and ammonia.

4. The process of claim 3, wherein the complexing agent is a catalyst for the reaction of the multi-functional isocyanate component with the aqueous polyol.

5. The process of claim 2, wherein the antimicrobial metallic compound is selected from silver saccharinate.

6. The process of claim 1, further comprising the step of adding a chain extender.

7. The process of claim 1, wherein the process effects a substantially uniform distribution of the antimicrobial metallic compound within the foam matrix during the process of making the antimicrobial polyurethane foam.

8. A method for producing a stable blend used in the manufacture of antimicrobial polyurethane materials, the method comprising:
    providing an aqueous polyol component;
    adding an antimicrobial metallic compound and a complexing agent to form a complex that is soluble in the aqueous polyol component; and
    solubilizing the antimicrobial metallic compound complex in the aqueous polyol component to form a stable blend, wherein the antimicrobial metallic compound complex of the stable blend is adapted, upon mixing with a multi-functional isocyanate component and reacting to form a polyurethane foam incorporating the antimicrobial metallic compound, to allow dissipation of the complexing agent such that the antimicrobial metallic compound is present as substantially only the antimicrobial metallic compound in the finished polyurethane foam.

9. The method of claim 8, wherein the antimicrobial metallic compound is a silver, zinc or copper compound.

10. The method of claim 8, wherein the complexing agent is selected from amine compounds, ammonium-containing compounds and ammonia.

11. The method of claim 8, wherein the complexing agent is a catalyst for the reaction of the multi-functional isocyanate component with the aqueous polyol.

12. An antimicrobial polyurethane foam produced according to the process of claim 1, the antimicrobial polyurethane foam comprising:
    a flexible matrix of polyurethane material defining a plurality of open cells; and
    an antimicrobial metallic material uniformly distributed throughout the matrix.

13. The antimicrobial foam of claim 12, further comprising silver nanoparticles that impart a permanent color to the foam in the visible portion of the UV-VIS spectrum without the use of a colorant wherein the color is not inherent to the reactive components used to produce the foam or is attributed to other additives or ingredients present in the foam.

14. The antimicrobial foam of claim 12, wherein the foam is hydrophilic, absorbent, and is resistant to discoloration by ambient light and is resistant to the discoloration induced by ethylene oxide (ETO) and electron beam (E-beam) irradiation sterilization processes.

15. The antimicrobial foam of claim 12, wherein the foam sustains antimicrobial activity against gram positive bacteria, gram negative bacteria and fungi for more than 7 days by releasing therapeutically effective amount of metal ions.

16. The antimicrobial foam of claim 13, wherein the foam is hydrophilic, absorbent, and is resistant to discoloration by ambient light and is resistant to the discoloration induced by ethylene oxide (ETO) and electron beam (E-beam) irradiation sterilization processes.

17. The antimicrobial foam of claim 13, wherein the foam sustains antimicrobial activity against gram positive bacteria, gram negative bacteria and fungi for more than 7 days by releasing therapeutically effective amount of metal ions.

18. An antimicrobial polyurethane foam produced according to the process of claim 1, the antimicrobial polyurethane foam comprising:
    a flexible matrix of polyurethane material defining a plurality of open cells; and
    antimicrobial silver nanoparticles uniformly distributed throughout the matrix,
    wherein the silver nanoparticles impart a permanent color to the foam in the visible portion of the UV-VIS spectrum without the use of a colorant wherein the color is not inherent to the reactive components used to produce the foam or is attributed to other additives or ingredients present in the foam.

* * * * *